United States Patent [19]

Cox et al.

[11] 4,225,394
[45] * Sep. 30, 1980

[54] RECLAMATION OF SPENT GLYCOL BY TREATMENT WITH ALKALI METAL HYDROXIDE AND DISTILLATION

[75] Inventors: Jerry W. Cox; Mulkey C. Wilkes, both of Beaumont, Tex.

[73] Assignee: PPG Industries, Inc., Pittsburgh, Pa.

[*] Notice: The portion of the term of this patent subsequent to Apr. 15, 1992, has been disclaimed.

[21] Appl. No.: 676,953

[22] Filed: Apr. 14, 1976

Related U.S. Application Data

[60] Continuation-in-part of Ser. No. 544,727, Jan. 28, 1975, abandoned, which is a division of Ser. No. 224,259, Feb. 7, 1972, Pat. No. 3,878,055, which is a continuation-in-part of Ser. No. 43,596, Jun. 4, 1970, abandoned.

[51] Int. Cl.$^2$ .................... B01D 3/00; C07C 29/24
[52] U.S. Cl. ..................... 203/37; 568/868; 203/18; 203/71
[58] Field of Search .............. 260/637 R; 203/37, 99, 203/71-85

[56] References Cited

U.S. PATENT DOCUMENTS

| | | | |
|---|---|---|---|
| 2,465,319 | 3/1949 | Whinfield et al. | 260/75 R |
| 2,614,072 | 10/1952 | Carlson | 203/37 |
| 2,727,882 | 12/1955 | Vodonik | 260/75 R |
| 2,788,373 | 4/1957 | Mills et al. | 260/637 R |
| 2,793,235 | 5/1957 | Jenkinson | 260/637 R |
| 3,367,847 | 2/1968 | Pierson | 260/637 R |
| 3,408,268 | 10/1968 | Pitts et al. | 260/637 R |
| 3,491,161 | 1/1970 | Pitts | 260/637 R |
| 3,525,774 | 8/1970 | Clarke | 260/637 R |
| 3,718,689 | 2/1973 | McCain et al. | 260/637 P |
| 3,878,055 | 4/1975 | Cox et al. | 203/37 |

*Primary Examiner*—Norman Yudkoff
*Attorney, Agent, or Firm*—Irwin M. Stein

[57] ABSTRACT

Ethylene glycol is recovered from spent glycol containing impurities, such as dimethyl terephthalate, by subjecting the spent glycol to a sequential flash evaporation-distillation or distillation-flash evaporation-distillation procedure. Dimethyl terephthalate impurities are rendered non-volatile by the addition of a small amount of alkali metal hydroxide prior to flash evaporation. Dewatering of spent glycol and separation of ethylene glycol from impurities rendered non-volatile by alkali metal hydroxide is also performed in one or two distillation steps. Sufficient ethylene glycol is recovered to make use of flash evaporation an optional step.

9 Claims, 2 Drawing Figures

RECLAMATION OF SPENT GLYCOL BY TREATMENT WITH ALKALI METAL HYDROXIDE AND DISTILLATION

CROSS-REFERENCE TO RELATED APPLICATIONS

This application is a continuation-in-part application of our copending U.S. application Ser. No. 544,727, filed Jan. 28, 1975 now abandoned, which application is a division of our application U.S. Ser. No. 224,259 filed Feb. 7, 1972, now U.S. Pat. No. 3,878,055, which in turn is a continuation-in-part application of our U.S. application Ser. No. 43,596 filed June 4, 1970, now abandoned.

DESCRIPTION OF THE INVENTION

In the manufacture of polyesters by the reaction of ethylene glycol with dimethyl terephthalate or terephthalic acid, residual glycol streams contaminated with impurities from the manufacturing process are recovered. This contaminated ethylene glycol is referred to in the trade as "spent glycol." As used herein, the term "spent glycol" is intended to mean and include the ethylene glycol recovered from processes for making and forming films and fibers of linear polyesters, particularly the high molecular weight linear polyesters made from ethylene glycol and terephthalic acid or its derivatives, such as dimethyl terephthalate. Approximately one-half of the ethylene glycol used in the polyesterification reaction is released in the monomer forming condensation step and is recovered in the spent glycol stream. Spent glycol, depending on its source, can contain from about 40 to about 98 weight percent ethylene glycol. Thus, the recovery of ethylene glycol from this stream plays an important role in the economics of polyester manufacturing.

The composition of spent glycol streams will vary depending upon the nature of the particular polyester making process from which the stream is derived and the particular phthalate reactant used, e.g., terephthalic acid or derivatives thereof. Principal among the contaminants present with the ethylene glycol (MEG) in the spent glycol are dimethyl terephthalate, salts of terephthalic acid, such as sodium terephthalate, methanol, water, acetals, such as acetaldehyde, higher glycols, such as diethylene glycol (DEG) and triethylene glycol (TEG), entrained monomer and other solid and liquid contaminants. Many of the solid and liquid contaminants in the spent glycol are unknown.

Depending on the source of the spent glycol, the concentrations of contaminants therein will vary widely. For example, spent glycol recovered from a process that uses dimethyl terephthalate might contain, as the principal contaminants, from a trace to 7 weight percent methanol and from 0.5 to 2.5 weight percent of water. In contrast, spent glycol recovered from a process using terephthalic acid may contain from 7 to 55 weight percent water.

Ethylene glycol that is recovered from the treatment of spent glycol can be used as a major component in antifreeze compositions or, if sufficiently pure, reused as the reactant in polyester manufacturing processes. It is particularly desirable to purify spent glycol to a sufficient purity so that it can be used interchangeably with virgin glycol in the production of polyesters.

Among the prior art methods suggested for recovering ethylene glycol from spent glycol, one involves the addition of about 25 weight percent water to the spent glycol followed by the separation of water, solids and methanol by distillation. See, for example, U.S. Pat. No. 3,408,268 and U.S. Pat. No. 2,788,373. The method proposed in U.S. Pat. No. 3,367,847 involves a first partial evaporation of the spent glycol, separation of the resulting slurry from the vapors, a second partial evaporation of that slurry, fractional distillation of the condensed vapors from the first partial evaporation step, and recycling of the condensed vapors from the second evaporation step to the first evaporator. In U.S. Pat. No. 3,491,161, aqueous solutions of ammonium hydroxide are added to spent glycol prior to distillation to convert the esters therein to amides and alcohols. Following addition of the ammonium hydroxide, the mixture is permitted to stand at ambient temperatures for periods of from one to two days to effect the conversion of the ester impurities. Water is then added to the mixture to facilitate the recovery of ethylene glycol by distillation.

While the methods described above are effective in upgrading spent glycol, they suffer from various shortcomings. The hold-up time in the method described in U.S. Pat. No. 3,491,161 detracts from that method. The method described in U.S. Pat. No. 3,408,268 has been reported to result in the formation of azeotropes of dimethyl terephthalate, and perhaps other esters in the spent glycol, with water during distillation. These azeotropes tend to plug transfer lines and heat exchangers, and foul pumps and other equipment in the distillation train. In addition, the water added to the spent glycol must also be evaporated, thereby increasing the heat requirements of the process. The method of U.S. Pat. No. 3,367,847 is performed on a small portion of the spent glycol stream and requires additional piping to accommodate the recycled stream.

It has now been discovered that spent glycol containing dimethyl terephthalate impurities can be upgraded by a combination of process steps, including: the addition of a small amount of alkali metal hydroxide, e.g., sodium hydroxide, to the spent glycol, flash evaporation of the thus treated spent glycol and distillation of the condensate from the flash evaporation step in one or more distillation zones. The mixture of spent glycol and alkali metal hydroxide is heated, if necessary, to a temperature of at least 30° C. It is believed that the alkali metal hydroxide catalyzes the reaction of dimethyl terephthalate with ethylene glycol to form the non-volatile hydroxyethyl ester, e.g., bis (2-hydroxyethyl) terephthalate. A temperature of at least 30° C. facilitates and promotes this reaction. In this manner, the dimethyl terephthalate impurity is prevented from vaporizing during flash evaporation and is removed with the non-volatile solids present in the spent glycol following the flash evaporation step. After the addition of alkali metal hydroxide thereto, the spent glycol is flash evaporated to provide a vaporous overhead and non-volatile (at the conditions of flash evaporation) bottoms. The overhead is condensed and subjected to distillation, usually in a fractional distillation zone, to provide a water-methanol overhead and a substantially dry and substantially solids-free glycol product as bottoms from near the bottom of the zone. If desired, the substantially dry and purified glycol bottoms can be further fractionally distilled to remove impurities not removed by the first distillation. The dry glycol overhead product from the second distillation is usually of sufficient purity to be used in the polyester manufacturing process.

In a further embodiment of the present invention, the spent glycol is first distilled in a dewatering column to remove water and methanol as an overhead product and ethylene glycol and non-volatile solids as a bottoms product. The bottoms product is flash evaporated and the vapors condensed and fractionally distilled to provide a substantially dry and pure glycol overhead product. Early removal of the water and methanol in this embodiment alleviates partially the burden on the evaporator.

In a further feature of this embodiment, a side stream of ethylene glycol is removed from near the bottom of the dewatering column. When a side product stream is taken from the column, dewatering of the spent glycol and separation of monoethylene glycol from non-volatile solids is accomplished in one column. The distillation in this one column can of course be conducted as a distillation in a plurality, e.g., two, of stages, such as in two columns. The monoethylene glycol removed as a side stream from the single distillation column is suitable for use as antifreeze grade monoethylene glycol. If additional purification is desired, the monoethylene glycol product stream can be further treated, e.g., by a further distillation, carbon bed treatment, or chemical treatment. Thus, alkali metal hydroxide treated spent glycol can be distilled in a single column (or in multiple columns for convenience) to recover a glycol stream having commercial utility. The bottoms fraction, which contains the non-volatile solids, can be discarded or treated to recover its monoethylene glycol content, e.g., by further distillation or flash evaporation and distillation of the condensed evaporator vapors. Similarly, the overhead from this column, which is principally water, can be discarded.

BRIEF DESCRIPTION OF THE DRAWINGS

A more complete understanding of the present invention will be had by reference to the attached drawings wherein.

DETAILED DESCRIPTION

In accordance with the instant invention, a method is provided for the recovery of substantially pure monoethylene glycol from spent glycol which is economical, simplified and rapid. In accordance with the instant invention and with particular reference to FIG. 1, tank 1 of suitable capacity is provided for spent glycol storage. The spent glycol in tank 1 is analyzed for dimethyl terephthalate and, if significant quantities thereof are detected, i.e., quantities of at least or greater than 0.1 percent by weight based on the spent glycol, alkali metal hydroxide is added to the tank from a source not shown, as indicated by line 21. The alkali metal hydroxide is added to the spent glycol before the spent glycol is flash evaporated. Thus, while the alkali metal hydroxide is shown being added to storage tank 1, it also can be metered into the spent glycol as it is being removed from storage tank 1 through line 20. Further, and with reference to FIG. 2, wherein like numerals indicate like features, the alkali metal hydroxide can be added to the bottoms product of dewatering colunm 3, e.g., in line 35 or into hold tank 9.

Any of the alkali metal hydroxides can be used in the present invention, e.g., sodium hydroxide, potassium hydroxide, lithium hydroxide, etc.; sodium hydroxide is readily available and is economically preferred. The amount of alkali metal hydroxide utilized to treat spent glycol containing significant amounts of dimethyl terephthalate is that amount which is sufficient to catalyze the reaction of substantially all of the dimethyl terephthalate present in the spent glycol with ethylene glycol but less than the amount required to saponify completely the dimethyl terephthalate content of the spent glycol, i.e., a catalytic amount. Typically, the amount of alkali metal hydroxide used will be at least 0.01 weight percent, based on the weight of spent glycol and calculated as alkali metal hydroxide. Generally, the alkali metal hydroxide will be employed in an amount of between about 0.01 and about 5 weight percent, preferably from about 0.02 to about 0.5 weight percent. Since the alkali metal hydroxide is used in catalytic amounts in the present process, rather than in reagent quantities, i.e., the quantity required to saponify the amount of dimethyl terephthalate in the spent glycol, this feature distinguishes the present process from related prior art methods.

Figure 1:
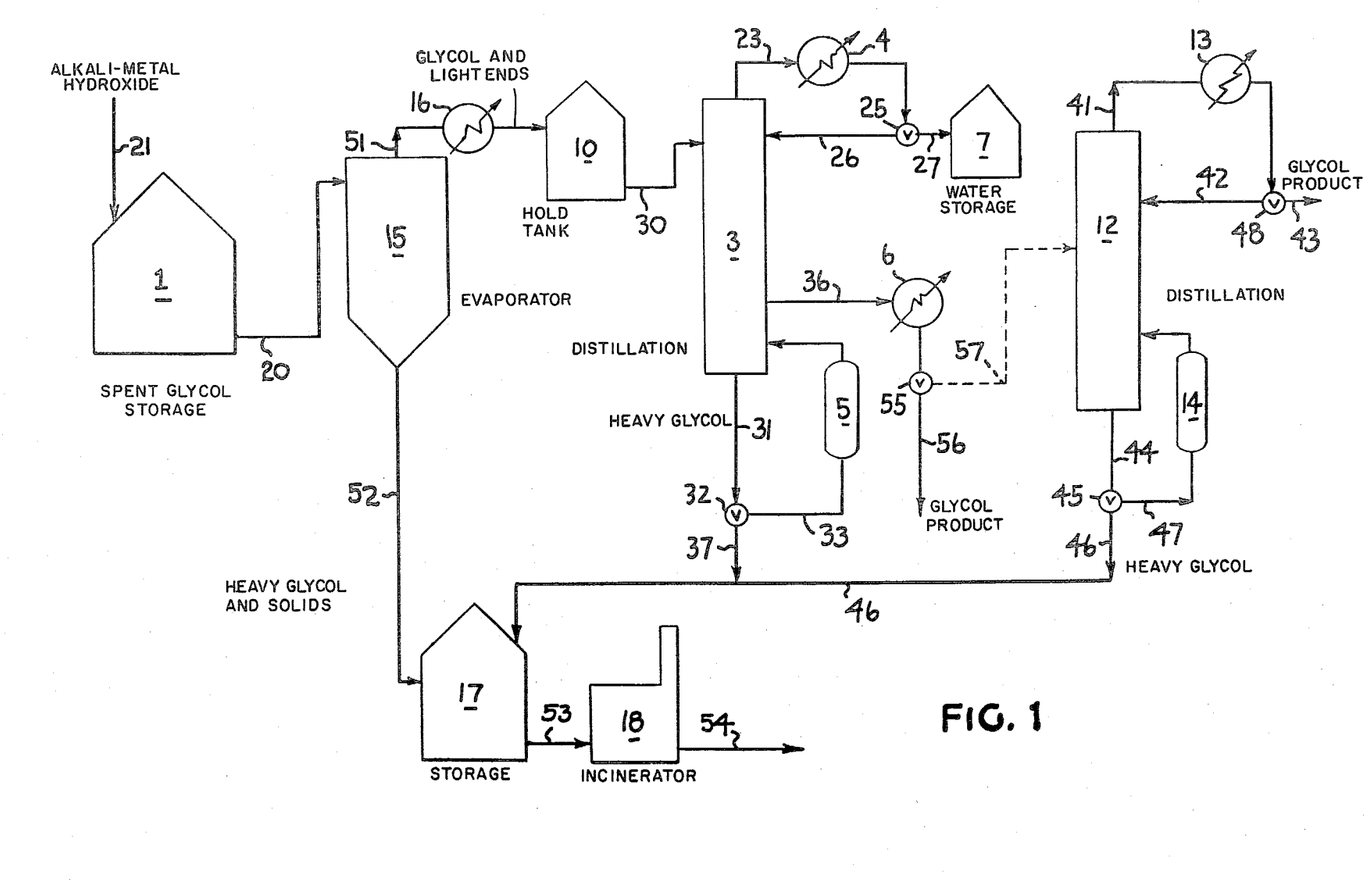
FIG. 1 is a schematic diagram of the process of the present invention.

The alkali metal hydroxide treated spent glycol can be heated to a temperature of at least 30° C. to promote the reaction of dimethyl terephthalate therein with ethylene glycol. While a temperature of at least 30° C. is typical at atmospheric pressure, such temperatures can range between 30° C. and 100° C. and are preferably between about 40° C. and about 60° C. Heat treatment can be provided by supplying internal or external heating means for storage tank 1 or by supplying heating means to one of the product transfer lines through which the alkali metal hydroxide treated spent glycol is conducted prior to flash evaporation. Typically, the treated spent glycol is maintained at at least 30° C. until dimethyl terephthalate has reacted with ethylene glycol, i.e., for at least 30 minutes. Naturally, the higher the preheat temperature, the less time required.

While not wishing to be bound by any particular theory, it is believed that the alkali metal hydroxide catalyzes the reaction of dimethyl terephthalate with ethylene glycol to form the monomeric bis (2-hydroxyethyl) terephthalate which is non-volatile at the conditions under which the spent glycol, or portions thereof, is treated subsequently, i.e., relatively non-volatile compared to ethylene glycol, methanol, water, etc. It has been found that by treating spent glycol with catalytic amounts of alkali metal hydroxide in the above-described manner, dimethyl terephthalate derivatives can be substantially separated from spent glycol by the techniques described herein, e.g. flash evaporation of the treated spent glycol stream, thereby avoiding the plugging and fouling problems caused by azeotropes of water and terephthalic acid or derivatives thereof.

Referring again to FIG. 1, the alkali metal hydroxide treated spent glycol is forwarded by line 20 to flash evaporator 15 which can be any of the conventional evaporators available in the market place. Flash evaporation can be conveniently accomplished in any of the so-called "thin film" evaporators which are commercially available. These evaporators utilize the agitated thin film principle of heat transfer. Rotating blades turning inside a cylinder spread the material to be processed in a thin film which is maintained under turbulence. These evaporators are characterized by low hold-up, short residence times and high heat transfer coefficients.

The feed rate to the flash evaporator is maintained sufficiently high to minimize the loss of ethylene glycol as bottoms from the flash evaporator. Typically, the flash evaporator is run under reduced pressures of approximately 4 to 100 millimeters of mercury absolute, e.g., 25 millimeters of mercury absolute pressure. Heat is typically furnished to the evaporator by any conventional means, e.g., a steam jacket, to provide evaporator wall temperatures of between 145° C. and about 165° C. For most effective results, feed rates to the evaporator will be in the range of from about 80 to about 180 grams of spent glycol per minute per 1.0 square foot of evaporator surface. The loss of ethylene glycol as bottoms is maintained at a minimum by operating under conditions such that little or no substantial accumulation of liquid is permitted to occur in the evaporator unit 15. Typically, the evaporator is run in a manner such that the bottoms from the evaporator are from about 50 to about 90 weight percent, e.g., 80 weight percent, solids.

The bottom fraction from evaporator 15 is forwarded by line 52 to heavy glycol and solids storage tank 17. From here, the material in storage tank 17 is forwarded by line 53 to liquid incinerator 18. The ashes formed in liquid incinerator 18 are removed through line 54 and discarded.

The overhead fraction from evaporator 15 is removed therefrom by line 51, consensed in condenser 16 and forwarded to hold tank 10. The contents of hold tank 10, which are principally a mixture of water and glycol, are forwarded by line 30 to a point above the midpoint of distillation column (still) 3 wherein the lower boiling water and methanol impurities are separated from the higher boiling impurities, such as the glycols and any solids and other non-volatiles remaining in the evaporator overhead. Drying column 3 can conveniently take any suitable form. Preferably, a tray column is used. The column can be operated at atmospheric pressure but is operated typically under a mild reduced pressure of 300 millimeters of mercury absolute pressure or less. Preferably, the column operates under a reduced pressure of 100 millimeters of mercury absolute pressure or less at the top of the column and a pot temperature of about 180° C. The overhead vapors from column 3 comprising principally the lower boiling impurities are removed from the column through line 23, condensed in condenser 4 and forwarded through valve 25 and line 27 to methanol and water storage tank 7. Reflux to column 3 is provided by valve 25 and line 26. The reflux ratio can be varied depending upon the location of the feed inlet, column conditions and the degree of purity desired for the ethylene glycol product. For ethylene glycol of 99.9 percent purity, by weight, a reflux ratio of 15:1 is usually sufficient; however, the higher the ratio, the purer the product. A reflux ratio of about 25:1 is preferred.

In the lower section of column 3, the higher boilers, i.e., essentially diethylene glycol and other higher glycols, together with residual solids and ethylene glycol, are removed by line 31. Part of the bottom stage liquid can be purged through valve 32 and lines 37 and 46 to storage tank 17. The remainder is fed through line 33 into reboiler 5 where it is partially vaporized and fed into the bottom of column 3. Reboiler 5 can be heated by any suitable external source, not shown, and its temperature and the flow through it are adjusted such that, at the reduced pressures of operation, it maintains the bottoms temperature in colunm 3 in the range of from 150° C. to 220° C. and the temperature of column 3 at the top in the range of from 48° C. to 90° C.

Ethylene glycol product is removed from column 3 as a vaporous bottoms side stream by line 36 which is located below the feed point and vertical center of the column. It is preferred that the product outlet line be about one-third of the column below the feed. This spacing permits the high boilers to be separated from the product. The ethylene glycol product side stream is condensed in condenser 6 and fed through valve 55 and line 56 to a suitable product storage tank, not shown.

If desired, and in order to further purify the ethylene glycol product, it can be distilled a second or additional times to insure complete removal of any solids or heavies present. As shown in FIG. 1 by broken line 57, ethylene glycol product is forwarded to a point slightly above the midpoint of distillation column 12. In this column, ethylene glycol product is removed as overhead and high boilers are removed as bottoms. Column 12 can also take any suitable form and preferably is also a tray column. The column is operated also under reduced pressure conditions, e.g., from about 10 to 100 millimeters of mercury absolute, pressure at the top of the column. Ethylene glycol vapors are removed from column 12 as overhead through line 41, condensed in condenser 13 and removed through valve 48 and line 43 to ethylene glycol product storage, not shown. After being condensed, part of the overhead is recirculated into column 12 through valve 48 and line 42 as reflux. A reflux ratio of about 2:1 is adequate to produce a substantially dry, pure monoethylene glycol product and to insure complete removal of any solids or heavies present in the product stream from column 3.

In the lower section of column 12, heavy boilers are removed through line 44. Part of the bottom stage liquid can be purged through valve 45 and line 46 to heavy glycol and solids storage tank 17. The remainder is fed through line 47 to reboiler 14 and into the bottom of column 12. Reboiler 14 can be heated by any suitable external source, not shown, and its temperature and the flow through it are adjusted such that, at the reduced pressures of operation, it maintains the bottoms temperature in column 12 in the range of from 150° C. to 210° C., e.g., 195° C. and a column temperature at the top of from 135° C. to 195° C. e.g., 180° C.

Figure 2:
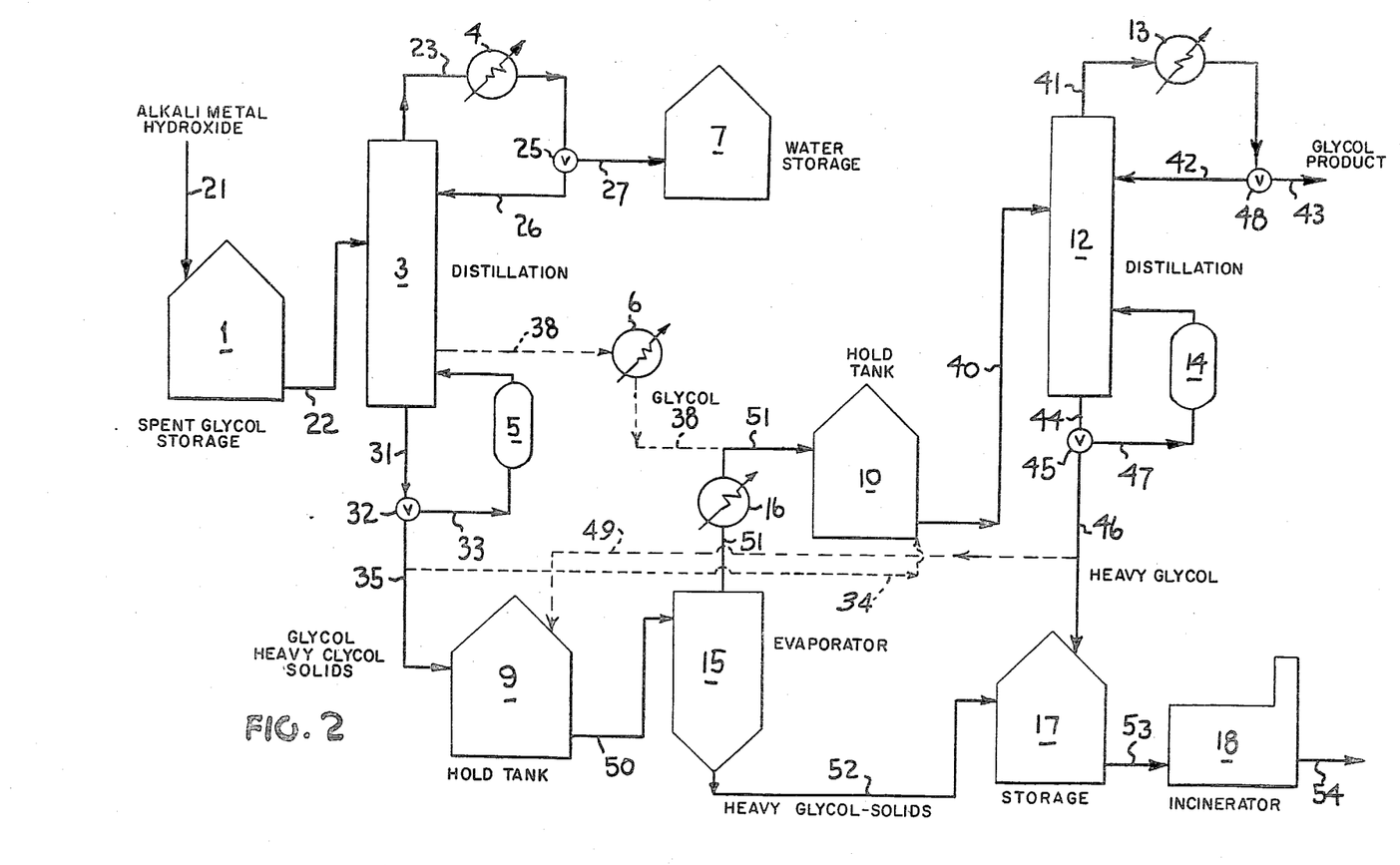
FIG. 2 is a schematic diagram of a preferred embodiment of the present invention wherein the spent glycol is distilled in a dewatering column before the flash evaporation and distillation steps.

Turning now to FIG. 2 wherein like numbers represent like features, there is shown a further embodiment of the present invention. In this embodiment, in lieu of flash evaporating all of the spent glycol, the spent glycol is first introduced into dewatering column 3 (usually slightly below the midpoint of the column), as shown by line 22. Water and methanol are removed from the column as an overhead volatile fraction and condensed and forwarded to storage tank 7. Ethylene glycol is removed from the column, along with high boilers as bottoms, through line 31, valve 32 and line 35 to evaporator hold tank 9. The contents of hold tank 9, i.e., dewatered spent glycol, are removed therefrom and forwarded through line 50 into flash evaporator 15. When spent glycol is dewatered before flash evaporation, the dewatering column can be operated at atmospheric pressure. This avoids the need for a chilled condensing system for this column, which would be necessary in order to condense and recover all the methanol in the overhead.

The overhead vapors from evaporator 15 are removed through line 51, condensed in condenser 16 and forwarded to hold tank 10. The glycol material in hold tank 10 is introduced into column 12 at slightly above the midpoint thereof by means of line 40. Ethylene glycol is separated from the higher boilers, such as diethylene glycol and residual solids, therein by fractional distillation. Substantially dry purified monoethylene glycol is removed from the top of the column, condensed and forwarded to product glycol storage in a manner already described.

If desired, a portion of the bottoms withdrawn from column 12 by line 44 and forwarded to heavy glycol and solids storage tank 17 cna be returned to evaporator hold tank 9, as shown by broken line 49, in order to recover a further portion of the monoethylene glycol remaining in the bottoms.

In a further embodiment of the invention illustrated by FIG. 2, a portion of the ethylene glycol charged to column 3 as spent glycol is removed from column 3 as a product side stream, as shown by broken line 38, condensed in condenser 6 and forwarded to glycol hold tank 10 through connecting means with line 51. This technique reduces the work load on evaporator 15.

As indicated, treatment of spent glycol containing dimethyl terephthalate or derivatives thereof with alkali metal hydroxide serves to fix such impurities, i.e., render them substantially non-volatile during conventional distillation of spent glycol. Such impurities are thereby removed with the so called non-volatile solids as the bottoms fraction from a distillation zone. This discovery also enables dewatering of spent glycol and separation of non-volatile impurities therefrom in a single distillation zone (without further chemical or physical steps) to provide ethylene glycol of at least antifreeze quality. The aforesaid ethylene glycol product is withdrawn from the column as a sidestream located below the feed point to the column and above the bottoms fraction draw point. If desired, the ethylene glycol product of antifreeze quality can be upgraded further by further treatment (chemical and/or physical) to thereby provide ethylene glycol of polyester manufacturing quality, i.e., fiber grade glycol.

To elaborate, reference is made to FIG. 1. Spent glycol treated with alkali metal hydroxide in tank 1 is forwarded directly to column 3 bypassing flash evaporator 15. Column 3 in this embodiment is similar to that described hereinbefore but larger. It is operated also in a substantially similar manner. More particularly, the treated spent glycol is introduced into the column at a point above the midpoint of the column, which is expected to contain about 40 trays. Since degradation of monoethylene glycol is minimized at lower pressures (and therefore lower temperatures), the column is operated at subatmospheric pressures. However, the lower the pressure in the column, the bigger the column required. Therefore, an economic tradeoff must be considered in the design of this column.

Bottom pressures contemplated for the column are between 75 and 100 mm. of mercury absolute. Temperatures at the bottom of the column are in the range of about 150°–205° C., e.g., 175° C. Top pressures contemplated for the column are between 10 and 100, e.g., 50, mm. of mercury absolute. Temperatures at the top of the column are in the range of 10° C.–55° C. Naturally, setting either the top or bottom operating conditions will regulate substantially the conditions at the opposite end of the column. Reflux ratios at the top of the column can vary depending on the purity of the ethylene glycol product desired; but, will tend to be at least 10:1.

The low boilers comprising water and methanol principally are withdrawn from the top of the column by line 23; while a stream comprising the high boilers, e.g., the higher glycols and non-volatile solids, are removed from the bottom of the column by line 31. The bottoms fraction will also contain some monoethylene glycol. The product stream of ethylene glycol is withdrawn from the column as side stream 36 at a point in the column below the spent glycol feed point. The distance between the feed point and product side stream withdrawal point should be sufficient to permit separation of the ethylene glycol from the high boilers.

The ethylene glycol product is of antifreeze quality. Antifreeze grade ethylene glycol is commonly at least 94 weight percent ethylene glycol and has a maximum APHA color of 10. The sidestream product in the aforesaid embodiment (and the product from the further embodiment described hereinafter) will contain at least 94 weight percent ethylene glycol, e.g., 99 weight percent ethylene glycol, and be substantially dry, i.e., contain less than 0.3 weight percent water. The water content is not critical for antifreeze grade because it is ultimately mixed with water. However, if the product is to be upgraded to fiber grade quality, the water content is important. The higher glycol content of the product can be controlled by the distillation conditions to contain as much as 5.0 weight percent, e.g., of diethylene glycol (DEG). Generally, the higher glycol content will be less than 0.3 weight percent. The product is substantially free of suspended solids. Thus, the ethylene glycol product produced by this embodiment can be substantially pure, dry and free of suspended solids.

Referring again to FIG. 1, if ethylene glycol of even higher purity, e.g., polyester grade, is desired, the product stream 36 can be introduced into column 12 by line 57 and distilled therein as previously described.

The use of a single continuous distillation to dewater and separate non-volatile solids from spent glycol can be conducted also in two connected stages, e.g., by splitting the function of the single column into two connected distillation columns. Use of two such columns provides versatility to the engineer operating the process. To elaborate, reference is made to FIG. 2.

Alkali metal hydroxide treated spent glycol from tank 1 is forwarded into column 3 which is operated at a top pressure of about 365 mm. of mercury absolute and a bottoms temperature of about 350° F. The reflux ratio at the top of the column is at least 10:1. Low boilers comprising mostly water and methanol are removed by line 23 from the top of the column, condensed and forwarded to storage tank 7. The dewatered bottoms from the column are removed through line 31 and forwarded directly to column 12 bypassing flash evaporator 15. Column 12 is operated at a top pressure of about 10 mm. of mercury absolute and a bottom temperature of about 112° C. The reflux ratio at the top of the column is about 1:1. Substantially pure monoethylene glycol is withdrawn from the top of column 12 through line 41; while the high boilers and non-volatile solids are withdrawn as the bottoms fraction by line 44. The solids content of the bottoms can be about 30 weight percent with the aforesaid embodiment.

For a more complete understanding of the instant invention, reference is made to the following examples which typify the operation of this invention on specific spent glycol streams. In the following examples, color and turbidity of a product are reported in APHA (American Public Health Association) units and Jackson turbidity units. Non-volatile residues are reported as NVR.

EXAMPLE I

A spent glycol was used having the following compositions:

| Spent Glycol Composition (% by weight) | |
|---|---|
| Methanol | 0.44 |
| Unknown | 0.06 |
| Water | 1.30 |
| MEG | 93.11 |
| DEG | 0.52 |
| Unknown | 0.01 |
| Unknown | 0.07 |
| TEG | 0.10 |
| Solids | 4.30 |
| Filterable Solids @ 23° C., 5μ Filter | 0.40 |
| Dimethyl Terephthalate | 0.40 |
| Chlorides, ppm | <3 |
| Properties | |
| pH, 100% | 2.3 |
| pH, 1:1 Mixture with water | 3.5 |
| Specific Gravity, 20/20° C. | 1.1169 |
| Ash | 0.0162 |

Because of the dimethyl terephthalate content, this sample was treated first with 0.02 percent NaOH by weight and heated to 40° C. prior to being fed to the flash evaporation step. This glycol was then flash evaporated in a one-quarter square foot Rototherm evaporator. The sample was fed to the evaporator at a rate of 14.7 grams per minute. The evaporator was operated under a reduced pressure of 58 millimeters of mercury with an overhead temperature of 132° C. and a steam jacket temperature of 155° C. The product recovered overhead had an analysis as follows:

| Composition (% by weight) | |
|---|---|
| Methanol | 0.60 |
| Unknown | — |
| Water | 1.53 |
| MEG | 97.34 |
| DEG | 0.47 |
| TEG | 0.06 |
| Properties | |
| pH | 6.1 |
| Color | 5 |
| Turbidity when 1:1 water mixture is made, no DMT crystals present | slight |

24.5 Percent of the material fed to the evaporator was lost as bottoms. The overhead product was fed to a 20-tray, 2-inch diameter Oldershaw column operating under a reduced pressure of 100 millimeters of mercury absolute. The product was fed to the fifth tray from the top of the column with the feed preheated to 130° C. Water and methanol were removed overhead and dry product was removed from the pot. The analysis of the dry product showed the following:

| Composition (% by weight) | |
|---|---|
| Water | 0.01 |
| MEG | 99.54 |
| DEG | 0.45 |
| Properties | |
| pH, 100% | 5.5 |
| pH, 1:1 Mixture with water | — |
| Color | 15 |
| Turbidity when 1:1 water mixture is made, no DMT crystals present | slight |

In order to obtain a complete removal of solids and heavies, the dried sample was then batch distilled in a 20-tray, 2-inch diameter Oldershaw column operating under a pressure of 10 millimeters of mercury absolute. A reflux ratio of 2 to 1 was maintained and the product was removed overhead. The finished product had the following analysis:

| Composition (% by weight) | |
|---|---|
| Water | 0.04 |
| MEG | 99.93 |
| DEG | 0.03 |
| Chlorides, ppm | <1 |
| Properties | |
| pH, 100% | 5.5 |
| pH, 1:1 Mixture with water | 5.7 |
| Specific Gravity, 20/20° C. | 1.1154 |
| Color | <5 |
| Acidity as acetic acid, % by weight | 0.001 |
| Turbidity of 1:1 water mixture | None |

EXAMPLE II

A spent glycol sample, which contained no measurable quantities of dimethyl terephthalate, was next purified. The sample had the following composition:

| Spent Glycol Composition (% by weight) | |
|---|---|
| Methanol | 0.09 |
| Unknown | 0.03 |
| Water | 0.35 |
| MEG | 96.80 |
| DEG | 0.59 |
| Unknown | <0.01 |
| Unknown | 0.01 |
| TEG | 0.08 |
| Solids | 2.03 |
| Filterable Solids @ 23° C., 5 μ Filter | 0.05 |
| Dimethyl Terephthalate | None |
| Chlorides, ppm | <3 |
| Properties | |
| pH, 100% | 2.2 |
| pH, 1:1 Mixture with water | 3.5 |
| Specific Gravity, 20/20° C. | 1.1165 |
| Ash | 0.0185 |

This sample was placed in a one-quarter square foot Rototherm evaporator. The material was fed to the evaporator at a high rate of feed (41.2 grams per minute). Evaporator reduced pressure of 57 millimeters of mercury absolute was utilized. The overhead temperature was maintained at 133° C. and a steam jacket temperature of 155° C. was used. The product was removed overhead and had the following analysis:

| Composition (% by weight) | |
|---|---|
| Methanol | 0.10 |
| Unknown | 0.07 |
| Water | 0.33 |
| MEG | 98.81 |
| DEG | 0.69 |
| TEG | — |

| Properties | |
|---|---|
| pH | 6.2 |
| Color | 5 |
| Turbidity when 1:1 water mixture is made, no DMT crystals present | None |
| Boiling Range (@ 760 mm. mercury) | |
| IBP, °C. | 183.0 |
| DP, °C. | 204.0 |

This product was then fed to a 20-tray, 2-inch diameter Oldershaw column operating under a reduced pressure of 100 millimeters of mercury absolute. The material was fed on the fifth tray from the top and had been preheated to 130° C. prior to feeding. Water and methanol were removed overhead and the dried product was removed from the pot as bottoms. The analysis of the bottoms product is as follows:

| Composition (% by weight) | |
|---|---|
| Water | 0.04 |
| MEG | 99.56 |
| DEG | 0.40 |
| Chlorides, ppm | 1 |

| Properties | |
|---|---|
| pH, 100% | 6.1 |
| pH, 1:1 Mixture with water | 5.7 |
| Color | 5 |
| Turbidity when 1:1 water mixture is made, no DMT crystals present | None |
| NVR, % by weight | 0.006 |
| Acidity as acetic acid, % by weight | 0.002 |
| Boiling Range (@ 760 mm. mercury) | |
| IBP, °C. | 196.5 |
| DP, °C. | 203.4 |
| Specific Gravity, 20/20° C. | 1.1155 |

To obtain complete removal of the solid materials, the above product was then fed to a second column which comprised a 20-tray, 2-inch diameter Oldershaw column. This column was operated under a reduced pressure of 10 millimeters of mercury absolute at a reflux ratio of 2 to 1. The product was removed overhead. The product recovered had the following composition:

| Composition (% by weight) | |
|---|---|
| Water | 0.04 |
| MEG | 99.88 |
| DEG | 0.08 |
| Chlorides, ppm | <1 |

| Properties | |
|---|---|
| pH, 100% | 6.6 |
| pH, 1:1 Mixture with water | 6.4 |
| Turbidity of 1:1 water mixture | None |
| Specific Gravity, 20/20° C. | 1.1153 |
| Color | <5 |
| Acidity as acetic acid, % by weight | 0.002 |
| Boiling Range (@ 760 mm. mercury) | |
| IBP, °C. | 196.6 |
| DP, °C. | 197.2 |

In a further embodiment of the instant invention, a distillation was carried out prior to the flash evaporation steps shown above in Examples I and II to avoid having to condense methanol in the flash evaporator overhead system. Thus, an initial distillation to remove water and methanol was conducted first.

The following Examples illustrate this embodiment.

EXAMPLE III

A spent glycol sample having the following composition was utilized in this experiment:

| Spent Glycol Composition (% by weight) | |
|---|---|
| Methanol | .52 |
| Unknown #1 | .13 |
| Water | 1.16 |
| Unknown #2 | — |
| MEG | 95.88 |
| DEG | .52 |
| Unknown #3 | .09 |
| Solids | 1.70 |

| Properties | |
|---|---|
| Ash | .011 |
| pH, 100% | 1.7 |
| pH, (50% water) | 3.1 |
| Specific Gravity 20/20° C. | 1.1154 |

This material was first distilled in a 1-inch diameter, 30-tray Oldershaw column operated at atmospheric pressure. The feed was preheated to approximately 100° C. and was fed between the tenth and eleventh trays from the top of the column. Water and methanol were removed as overhead, and product was taken from the pot. An analysis of overhead and bottoms taken from this column is as follows:

| Overhead Composition (% by weight) | |
|---|---|
| Methanol | 30.67 |
| Unknown #1 | 18.55 |
| Water | 49.46 |
| Unknown #2 | .61 |
| MEG | .71 |

| Bottoms Composition (% by weight) | |
|---|---|
| Water | .05 |
| MEG | 97.69 |
| DEG | .53 |
| Solids | 1.70 |

The bottoms product was then flash evaporated in a one-quarter square foot Rototherm evaporator to remove solids. The evaporator was operated under a reduced pressure of 10 millimeters of mercury using 60 psig saturated steam for heating. Approximately 5 percent by weight of the feed stock was lost as heavies in this step. The feed rate used varied between about 15 to 20 grams per minute.

The vaporized product removed from the evaporator was condensed and had the following analysis:

| Composition (% by weight) | |
|---|---|
| Water | .10 |
| MEG | 99.32 |
| DEG | .58 |
| Properties | |
| Color | <5 |

This product was then distilled in a 1-inch diameter, 20-tray Oldershaw column operating at a reduced pressure of 10 millimeters of mercury absolute with 1 to 2 reflux ratio. The finished product removed as overhead from this column had the following analysis:

| Composition (% by weight) | |
|---|---|
| Water | .10 |
| MEG | 99.85 |
| DEG | .05 |
| Properties | |
| Color | <5 |
| pH, 100% | 5.4 |
| pH (50% water) | 5.5 |
| Specific Gravity, 20/20° C. | 1.1156 |
| Acidity as acetic acid, % by weight | .002 |
| Boiling Range (@ 760 mm. mercury) | |
| IBP | 197.0 |
| 5% | 197.2 |
| 95% | 197.6 |
| DP | 197.8 |

EXAMPLE IV

A second run was made using a spent glycol having the following composition:

| Spent Glycol Composition (% by weight) | |
|---|---|
| Methanol | 3.61 |
| Unknown #1 | .10 |
| Water | .51 |
| Unknown #2 | .05 |
| MEG | 93.52 |
| DEG | .23 |
| Unknown #3 | — |
| Solids | 1.98 |
| Properties | |
| pH, 100% | 2.8 |
| pH (50% water) | 3.5 |
| Specific Gravity, 20/20° C. | 1.0977 |
| Ash | .067 |

This material was fed to a 1-inch diameter, 30-tray Oldershaw column which was operated at atmospheric pressure. The feed was preheated to 100° C. and fed between the tenth and eleventh trays from the top of the column. Water and methanol were removed overhead and product from the bottom of the column. The following is an analysis of both:

| Overhead Composition (% by weight) | |
|---|---|
| Methanol | 88.67 |
| Unknown #1 | 1.05 |
| Water | 9.78 |
| Unknown #2 | .49 |
| MEG | .01 |
| Bottoms Composition (% by weight) | |
| Water | .05 |
| MEG | 97.64 |
| DEG | .24 |
| Solids | 2.07 |

The bottoms product was fed to a flash evaporator. The evaporator was a one-quarter square foot Rototherm evaporator operated under a reduced pressure of 10 millimeters of mercury absolute and using 60 psig saturated steam in the jacket for heating. The feed rate to the evaporator varied between about 15 to 20 grams per minute. The recovered vaporized product had the following composition:

| Composition (% by weight) | |
|---|---|
| Water | .10 |
| MEG | 99.52 |
| DEG | .38 |
| Properties | |
| Color | <5 |

This product was fed to a 1-inch diameter, 20-tray Oldershaw column operating at a reduced pressure of 10 millimeters of mercury absolute. The final product removed as overhead from this still had the following composition:

| Composition (% by weight) | |
|---|---|
| Water | .10 |
| MEG | 99.86 |
| DEG | .04 |
| Properties | |
| Color | <5 |
| pH, 100% | 5.1 |
| pH, (50% water) | 5.1 |
| Specific Gravity, 20/20° C. | 1.1156 |
| Acidity as acetic acid, % by weight | .003 |
| Boiling Range (@ 760 mm. mercury) | |
| IBP | 197.1 |
| 5% | 197.2 |
| 95% | 197.6 |
| DP | 198.0 |

EXAMPLE V

With reference to FIG. 2, spent glycol obtained from the manufacture of polyesters from ethylene glycol and dimethyl terephthalate and containing about 0.4 weight percent dimethyl terephthalate is treated with 0.02 weight percent sodium hydroxide, as NaOH, in storage tank 1. The approximate spent glycol composition in weight percent is as follows: 96.9 percent glycols, 1.0 percent water, 0.4 percent methanol and about 1.7 percent solids and non-volatiles. The treated spent glycol is removed from storage tank 1 and fed at a temperature of about 16° C. into column 3 near the bottom of the rectifying section of the column. Column 3 is a tray-type distillation column and is operated under a reduced pressure of about 300 millimeters of mercury absolute pressure at the top of the column. Reboiler 5 maintains a pot temperature of about 177° C. The overhead vapors from column 3 are removed through line 23, condensed in condenser 4 and forwarded to methanol-water storage tank 7. The composition of the overhead condensate stream is about 70 weight percent water and about 30 weight percent methanol. An ethylene glycol product side stream is removed from near the bottom of the column and below the feed point through line 38, condensed in condenser 6 and forwarded to glycol hold tank 10. The composition of the product stream is about 99.3 weight percent monoethylene glycol, about 0.6 weight percent diethylene glycol and high boilers and about 0.1 weight percent water.

The bottoms from column 3 are forwarded through lines 31 and 35 into evaporator hold tank 9. The bottoms comprise approximately 79 weight percent monoethylene glycol, 1 weight percent diethylene glycol and higher boilers, about 0.05 weight percent water and about 20 weight percent solids and non-boilers. This material is forwarded through line 50 to flash evaporator 15 from which an overhead comprising about 99.8 weight percent monoethylene glycol, about 0.1 weight percent diethylene glycol and higher boilers, and about 0.06 weight percent water are removed. This overhead product is condensed in condenser 16 and mixed with the ethylene glycol product side stream previously removed from column 3 in glycol hold tank 10.

The contents of hold tank 10, which are about 99.4 weight percent monoethylene glycol, about 0.6 weight percent diethylene glycol and higher boilers, and about 0.1 weight percent water is introduced into column 12 slightly above the midpoint of the column.

Column 12 is operated under a reduced pressure of about 10 millimeters of mercury absolute pressure at the top of the column. Reboiler 14 maintains the pot temperature in column 12 at about 195° C. The ethylene glycol vaporous overhead from column 12 is removed through line 41, condensed in condenser 13 and removed to storage, not shown, by means of line 43. The approximate composition of the product is 99.89 weight percent monoethylene glycol, about 0.01 weight percent diethylene glycol, and about 0.10 weight percent water.

The bottoms from evaporator 15, which comprise about 16 weight percent monoethylene glycol, about 4 weight percent diethylene glycol and higher boilers, and about 80 weight percent solids and non-volatiles, is forwarded to storage tank 17 where it is mixed with the bottoms from column 12, which comprises about 77 weight percent monoethylene glycol and about 23 weight percent diethylene glycol. The contents of storage tank 17 are introduced into liquid incinerator 18 by line 53 and burned. The ashes from incinerator 18 are removed by line 54 and discarded.

EXAMPLE VI

Referring again to FIG. 2, spent glycol obtained from the manufacture of polyesters from ethylene glycol and terephthalic acid are stored in storage tank 1. No dimethyl terephthalate is found in the spent glycol and thus no alkali metal hydroxide is added to the spent glycol. The spent glycol feed is removed from storage tank 1 by line 22 and introduced at about 16° C. into column 3 at about the midpoint of the column. Drying column 3 operates under the same conditions as that described with respect to Example V. The approximate composition of the spent glycol feed is about 45 weight percent glycol (as MEG), about 52 weight percent water and about 3 weight percent solids and non-volatiles. The overhead from the drying column is about 99.99 weight percent water and about 0.01 weight percent monoethylene glycol. The glycol content of the overhead is so slight that the overhead condensate can be directly sewered. However, a portion of the overhead condensate is returned to the column as reflux.

An ethylene glycol product side stream is removed through line 38, condensed in condenser 6 and forwarded to hold tank 10. The product side stream is approximately 99.99 weight percent glycol (as MEG) and about 0.1 weight percent water. The bottoms from column 3 comprise about 80 weight percent glycol (as MEG) and about 20 weight percent solids and non-volatiles with very small amounts, e.g., about 0.05 weight percent water. These bottoms are forwarded to evaporator feed tank 9 by line 35 and from there introduced into evaporator 15. The overhead vapors from evaporator 15 are condensed in condenser 16 and mixed with the ethylene glycol product side stream in glycol hold tank 10. The approximate composition of the evaporator overhead is about 99.9 weight percent glycol (as MEG) and about 0.1 weight percent water. The contents of glycol hold tank 10, which comprise about 99.3 weight percent monoethylene glycol, about 0.6 weight percent diethylene glycol and about 0.1 weight percent water is introduced into distillation column 12 at slightly above the midpoint of the column. The column is operated at the same conditions described in Example V. The vaporous overhead from column 12 is condensed and forwarded to storage. The approximate composition of the product is about 99.89 weight percent monoethylene glycol, about 0.01 weight percent diethylene glycol and about 0.10 weight percent water.

The bottoms from evaporator 15, which comprise about 20 weight percent glycol (as MEG) and about 80 weight percent solids and non-volatiles, are forwarded to storage tank 17 where it is mixed with the bottoms from column 12, which are about 77 weight percent monoethylene glycol and about 23 weight percent diethylene glycol. The combined contents of storage tank 17 are introduced into liquid incinerator 18 and the ashes therefrom are removed and discarded, as shown by line 54.

EXAMPLE VII

Referring again to FIG. 2, 47,890 pounds of spent glycol in tank 1 having a pH of 3.3 was treated with sodium hydroxide until the pH was raised to 8.1. The pH adjusted spent glycol was charged to distillation column 3 having 18 trays at a rate of 1.53 gallons/minute. The pressure at the top of column 3 was 365 millimeters mercury absolute and the temperature at the bottom of the column was 350° F. (177° C.). The temperature at the top of column 3 was approximately 175° F. (79° C.) and the reflux ratio was about 10:1. The spent glycol had the following composition:

| Spent Glycol Composition (% by weight) | |
|---|---|
| Water | 4.70 |
| Methanol | 0.04 |
| MEG[1] | 88.32 |
| DEG[1] | 0.77 |
| TEG[1] | 0.31 |

| Spent Glycol Composition (% by weight) | |
|---|---|
| Solids[2] | 5.84 |

[1]Monoethylene glycol (MEG); Diethylene glycol (DEG) Triethylene glycol (TEG).
[2]Includes dimethyl terephthalate and derivatives thereof and dissolved solids.

The overhead stream from the column taken by line 27 to storage amounted to about 1390 pounds and had the following composition:

| Overhead Composition (% by weight) | |
|---|---|
| Water | 99.84 |
| Methanol | 0.13 |
| MEG | 0.03 |

The bottoms from column 3 were removed by line 31 and forwarded directly to column 12, which had 20 trays and was operated at a top pressure of 9.5 millimeters of mercury absolute. The temperature at the bottom of the column was 236° F. (113° C.). The temperature at the top of the column was 202° F. (94° C.). The reflux ratio at the top of the column was about 1:1. The product stream was taken as an overhead fraction. It amounted to about 37,550 pounds and had the following composition:

| Product Composition (% by weight) | |
|---|---|
| MEG | 99.56 |
| Water | 0.16 |
| DEG | 0.23 |

The bottoms from column 12 removed by line 44 amounted to about 8,950 pounds and had the following composition:

| Bottoms Composition (% by weight) | |
|---|---|
| Water | 0.19 |
| MEG | 58.36 |
| DEG | 9.26 |
| TEG | 0.94 |
| Solids | 31.25 |

This data of this example shows that alkali metal hydroxide treated spent glycol can be dewatered and separated from non-volatile solids by a single continuous distillation conducted as a plural (two stage) distillation.

As will be readily appreciated from the above, substantial purification of spent glycol can be obtained by utilization of the combination of the flash evaporation and distillation techniques described above. In those instances where at least 0.1 percent by weight dimethyl terephthalate is present in the spent glycol to be treated, a simple alkali metal hydroxide treatment prior to the flash evaporation step prevents dimethyl terephthalate derivatives from being carried with the overhead in the distillation step and thereby possibly plug lines and other equipment in the distillation column overhead train. In those embodiments where it is desired to remove methanol and water prior to conducting the flash evaporation step, the alkali metal hydroxide treatment can occur prior to or during that step. The purification or upgrading process can be easily utilized in conjunction with the operation of an esterification process for the purpose of recovering spent glycol and thus render the esterification process more economical.

While the invention has been described with reference to certain specific examples and illustrative embodiments, it is, of course, not intended to be so limited except insofar as appears in the accompanying claims.

We claim:

1. A method for recovering ethylene glycol from spent glycol containing at least 0.1 weight percent dimethyl terephthalate, comprising the sequential steps of:
    (a) treating the spent glycol at at least 30° C. with about 0.02 weight percent alkali metal hydroxide based on the spent glycol, said amount of alkali metal hydroxide being sufficient to catalyze the reaction of dimethyl terephthalate with ethylene glycol to form high boilers but insufficient to saponify completely the dimethyl terephthalate;
    (b) and distilling the said alkali metal hydroxide treated spent glycol to recover;
        (1) a stream of low boilers comprising water as an overhead fraction,
        (2) a product stream of antifreeze quality ethylene glycol, and
        (3) a stream of high boilers including ethylene glycol as a bottoms fraction.

2. The method of claim 1 wherein distillation is conducted in one distillation column and the product stream is withdrawn as a side stream from the column at a point below the spent glycol feed point.

3. The method of claim 2 wherein the side product stream is at least 99 weight percent ethylene glycol.

4. The method of claim 1 wherein the spent glycol is treated with alkali metal hydroxide at from 30° C. to 110° C. for at least 30 minutes before distillation.

5. The method of claim 4 wherein the alkali metal hydroxide is sodium hydroxide.

6. A method for recovering ethylene glycol from spent glycol containing at least 0.1 weight percent dimethyl terephthalate, comprising the sequential steps of:
    (a) treating the spent glycol at at least 30° C. with about 0.02 weight percent alkali metal hydroxide based on the spent glycol, said amount of alkali metal hydroxide being sufficient to catalyze the reaction of dimethyl terephthalate with ethylene glycol to form high boilers but insufficient to saponify completely the dimethyl terephthalate; and
    (b) distilling alkali metal hydroxide treated spent glycol by:
        (1) introducing treated spent glycol into a first distillation column and removing therefrom an overhead fraction of low boilers comprising principally water,
        (2) removing dewatered spent glycol as a bottoms fraction from the first column,
        (3) forwarding directly dewatered spent glycol from the said first column to a second distillation column,
        (4) removing an overhead product stream of antifreeze quality ethylene glycol from the said second column, and
        (5) removing a stream of high boilers including ethylene glycol as a bottoms product from the said second column.

7. The method of claim 6 wherein the overhead product stream from the second column is at least 99 weight percent ethylene glycol.

8. The method of claim 6 wherein the spent glycol is treated with alkali metal hydroxide at from 30° C. to 110° C. for at least 30 minutes before distillation.

9. The method of claim 8 wherein the alkali metal hydroxide is sodium hydroxide.

* * * * *